United States Patent [19]

Watkins

[11] Patent Number: 5,688,770
[45] Date of Patent: Nov. 18, 1997

[54] ANTIGLAUCOMA COMPOSITIONS AND METHODS

[75] Inventor: Robert W. Watkins, Great Meadows, N.J.

[73] Assignee: Schering Corporation, Kenilworth, N.J.

[21] Appl. No.: 224,620

[22] Filed: Apr. 7, 1994

Related U.S. Application Data

[62] Division of Ser. No. 450,766, Dec. 14, 1989, Pat. No. 5,326,750.

[51] Int. Cl.$^6$ .................... A61K 37/14; A61K 37/16; A61K 38/16; A61K 38/08
[52] U.S. Cl. .................... 514/16; 514/2; 514/3; 514/4; 514/5; 514/6; 514/7; 514/8; 514/9; 514/10; 514/11; 514/12; 514/13; 514/14; 514/15; 514/236.2; 514/913
[58] Field of Search ................ 514/2, 3, 4, 5, 514/6, 7, 8, 9, 10, 11, 12, 13, 14, 15, 16, 913, 236.6

[56] References Cited

U.S. PATENT DOCUMENTS

| | | |
|---|---|---|
| 3,985,875 | 10/1976 | Hayaski, et al. . |
| 4,185,096 | 1/1980 | Castro et al. . |
| 4,269,827 | 5/1981 | Burton et al. . |
| 4,384,994 | 5/1983 | Veber et al. . |
| 4,424,207 | 1/1984 | Szelke et al. . |
| 4,455,303 | 6/1984 | Burton . |
| 4,470,971 | 9/1984 | Boger et al. . |
| 4,477,440 | 10/1984 | Boger et al. . |
| 4,477,441 | 10/1984 | Boger et al. . |
| 4,478,826 | 10/1984 | Veber et al. . |
| 4,478,827 | 10/1984 | Haber et al. . |
| 4,479,941 | 10/1984 | Veber et al. . |
| 4,481,192 | 11/1984 | Cazaubon et al. . |
| 4,485,099 | 11/1984 | Boger et al. . |
| 4,510,085 | 4/1985 | Hansen, Jr., et al. . |
| 4,514,332 | 4/1985 | Hansen, Jr., et al. . |
| 4,574,127 | 3/1986 | Baldwin et al. . |
| 4,602,093 | 7/1986 | Baldwin et al. . |
| 4,749,698 | 6/1988 | Neiss et al. . |
| 4,906,613 | 3/1990 | Watkins . |
| 5,036,048 | 7/1991 | Watkins . |
| 5,352,666 | 10/1994 | Watkins . |

FOREIGN PATENT DOCUMENTS 0114333  8/1984  European Pat. Off. .

OTHER PUBLICATIONS

Hypertension 6 (Supp I): I–111, 1984.
Science 175: 656, 1972.
J Pharm Exp. Ther. 203: 485, 1977.
R.R. Luther, et al., Renin Inhibitors: Specific Modulators of the Renin–Angiotensin system, Arzneim–Forsch/Drug Res. 39(1), Nr.1 (1989), pp. 1–5.
Miguel A. Ondetti, et al., Inhibition of the Renin–Angiotensin System. A New Approach to the Therapy of Hypertension, Journal of Medicinal Chemistry vol. 24, No. 4, 4/81, pp. 355–361.
Ionitesu, Oftalmologia vol. 26, No. 2, (1982) pp. 137–138.
Hypertension 4 (Suppl II): II–59, 1982.
Biochem. J. 205: 43, 1982.
Biochem. Biophys. Res. Commun. 97(1): 230, 1980.
Biochem. Biophys. Res. Commun. 118(3): 929, 1984.
Biochemistry 12: 3877, 1973.
Biochemistry 14: 3892, 1975.
Nature 303: 81, 1983.
Nature 299: 555, 1982.
Peptides: Structure and Function, ed V.J Hruby, Rockford, Illinois, Pierce Chemical Co., 1984.
Proc. Natl. Acad. Sci. USA 81: 48, 1984.
Biochem. Biophys. Res. Commun. 100: (1) 177, 1981.
J. Clin. Endocrinol. 27: 699, 1967.
Biochem. Parmacol. 20: 914, 1971.
Proc. Soc. Exp. Biol. Med. 155: 468, 1977.
Am. J. Physiol. 234(6): E 593, 1978.
Biochemistry 19: 2616, 1980.
J. Chem. Soc. Chem. Commun: 109, 1985.
Kokubu, et al., Hypertension: 7(3): 837, (1985).
Luly, et al., Pharmacologist 27(3): 260, 1985.
Biochem. Biophys. Res. Commun. 54: 1356, 1973.

*Primary Examiner*—Zohreh Fay
*Attorney, Agent, or Firm*—Joseph T. Majka

[57] ABSTRACT

The present invention relates to ophthalmo-logical pharmaceutical compositions comprising a renin inhibitor and to methods for using said composition in the treatment of glaucoma.

3 Claims, No Drawings

ANTIGLAUCOMA COMPOSITIONS AND METHODS

This is a division of U.S. application Ser. No. 07/450,766 filed Dec. 14, 1989, now U.S. Pat. No. 5,326,750.

BACKGROUND OF THE INVENTION

Glaucoma is an ocular disease complex associated with an elevated pressure within the eye (i.e., intraocular pressure, IOP). As a result of the elevated IOP, damage to the optic nerve resulting in irreversible loss of visual function may ensue. Untreated, this condition may eventually lead to blindness.

Ocular hypertension, i.e., the condition of elevated intraocular pressure without optic nerve damage or characteristic glaucomatous visual field loss, is now believed by the majority of opthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine, used as a topical solution, must be utilized cautiously in patients with high blood pressure, diabetes, hyperthyroidism and cerebral artereosclerosis due to the possibility of systemic action.

Timolol, a clinically utilized, topically applied agent for lowering intraocular pressure, must be used with caution in patients in whom beta-adrenergic blockage may be undesirable. Systemic absorption of topically administered timolol and systemic beta-blockade are responsible for the contraindication of timolol therapy for glaucoma in patients with compromised pulmonary function and in patients who cannot tolerate its systemic cardiovascular action.

Pilocarpine, a topical drug, although considered systemically harmless and quite effective, may cause considerable local difficulties. Pupillary constriction causes the eye to lose its ability to adapt from light to dark. Accommodation may become stimulated so that the patient's refraction is sometimes incorrect and vision becomes blurred. The drug itself may cause a local vasodilation and red dyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and general malaise. European Patent Application 81400326.5, Publication number 36,351 attempts to overcome these difficulties by the topical administration of an alkali metal salt of a carbonic anhydrase inhibitor.

The present invention provides a new composition and method for reducing and controlling elevated intraocular pressure, especially the elevated IOP associated with glaucoma.

SUMMARY OF THE INVENTION

The invention sought to be patented in its pharmaceutical composition aspect is a topical ophthalmologically acceptable composition useful for reducing and controlling elevated intraocular pressure, especially elevated IOP associated with glaucoma, which comprises a renin inhibitor in combination with an ophthalmologically acceptable carrier for topical use.

The invention sought to be patented in its pharmaceutical method aspect is a method for reducing and controlling the elevated intraocular pressure associated with glaucoma or that resulting from use of steroidal anti-inflammatory drugs in a mammal, e.g., a human, which method comprises administering to said mammal an effective amount of the above-defined pharmaceutical composition.

DESCRIPTION OF THE INVENTION

Examples of renin inhibitors include, but are not limited to, the following substances, which are disclosed in the indicated publications:

| Renin Inhibitor | Reference Citing Renin Inhibition |
|---|---|
| Iva His Pro Phe His Sta Leu Phe | Hypertension 6 (Suppl I): I-111, 1984 |
| Pepstatin | Science 175: 656, 1972 |
| 2-[4-(4'-chlorophenoxy)-phenoxyacetyl-amino]ethyl-phosphoryl ethanolamine (PE 104) | J Pharm Exp. Ther. 203: 485, 1977 |
| 1-1-D—His Pro Phe His—NH—CH(CH$_2$CH(CH$_3$)$_2$)—CH$_2$—Leu—Val Tyr | Hypertension 4 (Suppl II): II-59, 1982 |
| Cys His Pro Phe His Cys Leu Val Tyr Ser (disulfide bridge Cys-Cys) | Biochem. J. 205: 43, 1982 |
| Lys Cys His Pro Phe His Cys Leu Val—Tyr Ser (disulfide bridge) | " |
| Cys His Pro Phe His Cys Leu Val Tyr Lys (disulfide bridge) | " |
| Lys Cys His Pro Phe His Cys Val Ile—His Ser (disulfide bridge) | " |
| Pro His Pro Phe His Phe Phe Val Tyr Lys | Biochem. Biophys. Res. Commun. |

| Renin Inhibitor | Reference Citing Renin Inhibition |
|---|---|
| | 97(1): 230, 1980 |
| Z—His Pro Phe His Leucinal | Biochem. Biophys. Res. Commun. 118(3): 929, 1984 |
| (Benzyloxycarbonyl equals Z) | |
| Z—Pro Phe His Leucinal | Biochem. Biophys. Res. Commun. 118(3): 929, 1984 |
| Z—Phe His Leucinal | Biochem. Biophys. Res. Commun. 118(3): 929, 1984 |
| Z—His Leucinal | Biochem. Biophys. Res. Commun. 118(3): 929, 1984 |
| Z-[3-(1'-naphthyl)Ala]His Leucinal | Biochem. Biophys. Res. Commun. 118(3): 929, 1984 |
| His Pro Phe His D—Leu Leu Val Tyr | Biochemistry 12: 3877, 1973 |
| Asp Arg Val Tyr Ile His Pro Phe His-Leu Leu Val Tyr Ser | Biochem. Biophys. Res. Commun. 54: 1365, 1973 |
| Pro His Pro Phe His Phe Phe Val Tyr | Biochemistry 14: 3892, 1975 |
| D—His Pro Phe His Leu$^{R*}$ Leu Val Tyr | Hypertension 4 (Suppl II): II-59, 1982 |
| Boc—His Pro Phe His Sta Leu Phe | Nature 303: 81, 1983 |
| Pro His Pro Phe His Leu$^{R*}$ Val Ile His Lys | Nature 299: 555, 1982 |
| Iva His Pro Phe His Sta Ile Phe | Nature 303: 81, 1983 |
| Boc Phe His Sta Ala Sta | Peptides: Structure and Function ed V. J. Hruby Rockford, Illinois, Pierce Chemical Co., 1984 |
| Arg Ile Pro—OMe | Proc. Natl. Acad. Sci. USA 81: 48, 1984 |
| Boc—Leu Lys Lys Met Pro—OMe | Proc. Natl. Acad. Sci. USA 81: 48, 1984 |
| Boc—Arg Ile Pro Leu Lys Lys Met Pro—OMe | Proc. Natl. Acad. Sci. USA 81: 48, 1984 |
| Boc—Glu Arg Ile Pro Leu Lys Lys Met Pro—OMe | Proc. Natl. Acad. Sci. USA 81: 48, 1984 |
| Ac Val Val Sta Ala Sta | Proc. Natl. Acad. Sci. USA 81: 48, 1984 |
| Iva Val Val Sta Ala Sta Glu | Proc. Natl. Acad. Sci. USA 81: 48, 1984 |
| L-α-hydroxy—isocaproyl—Leu Val Phe—OMe | Biochem. Biophys. Res. Commun. 100: (1) 177, 1981 |
| L-α-hydroxyisovaleryl Leu Phe—OMe | Biochem. Biophys. Res. Commun. 100: (1) 177, 1981 |
| L-α-hydroxyisovaleryl Leu Val Phe—OMe | Biochem. Biophys. Res. Commun. 100: (1) 177, 1981 |
| L-α-hydroxyisovaleryl Leu Val Phe($NO_2$)—OMe | Biochem. Biophys. Res. Commun. 100: (1) 177, 1981 |
| L-α-hydroxy-isovaleryl Leu Val Tyr(Me)—OMe | Biochem. Biophys. Res. Commun. 100: (1) 177, 1981 |
| L-α-hydroxy-isovaleryl Leu Val Phe($NH_2$)—OMe | Biochem. Biophys. Res. Commun. 100: (1) 177, 1981 |
| Lac Leu Val Phe($NO_2$)—OMe | Biochem. Biophys. Res. Commun. 100: (1) 177, 1981 |
| Lac Leu Val Tyr(Me)—OMe | Biochem. Biophys. Res. Commun. 100: (1) 177, 1981 |
| Lac Leu Val Phe($NH_2$)—OMe | Biochem. Biophys. Res. Commun. 100: (1) 177, 1981 |
| H—Leu Val Phe($NO_2$)—OMe | Biochem. Biophys. Res. Commun. 100: (1) 177, 1981 |
| H—Leu Val Tyr(Me)—OMe | Biochem. Biophys. Res. Commun. 100: (1) 177, 1981 |
| Heparin | J. Clin. Endocrinol. 27: 699, 1967 |
| Deoxycholic acid | Biochem. Pharmacol. 20: 914, 1971 |
| Phosphotidyl ethanolamine where acid substituents thereof are each independently arachidonic acid, linolenic acid or stearic acid | Proc. Soc. Exp. Biol. Med. 155: 468, 1977 |
| Capric acid | Am. J. Physiol. 234(6): E 593, 1978 |
| Lauric acid | " |
| Palmitoleic acid | " |
| Linoleic acid | " |
| Arachidonic acid | " |
| $N_2$Ac Ile—$OCH_3$ | Biochemistry 19: 2616, 1980 |
| $N_2$Ac Leu—$OCH_3$ | " |
| 1,2-epoxy-3-(p-nitrophenoxy)propane | |
| Sta Leu Phe | Nature 303: 81, 1983 |
| His Sta Leu Phe | " |
| Phe His Sta Leu Phe | " |
| Pro Phe His Sta Leu Phe | " |
| Ibu His Pro Phe His Sta | " |

-continued

| Renin Inhibitor | Reference Citing Renin Inhibition |
|---|---|
| Ibu His Pro Phe His Sta Leu | " |
| Ibu His Pro Phe His Sta Leu Phe | " |
| Ibu His Pro Phe His Sta Ala Phe | " |
| Ibu His Pro Phe His Sta Val Phe | " |
| Ibu His Pro Phe His Sta Ile Phe | " |
| Boc His Pro Phe His Sta Leu Tyr | " |
| Boc His Pro Phe His Sta Leu Phe—OCH₃ | " |
| Iva His Pro Phe His Sta Leu Val Phe | " |
| POA Leu Sta Val Phe—OCH₃ (POA equals phenoxyacetyl) | " |
| POA Leu Sta Leu Phe—OCH₃ | " |
| POA His Sta Leu Phe—OCH₃ | " |
| Iva His Pro Phe His Leu Sta Val Phe | " |
| Iva His Pro Phe His Sta Leu Phe | " |
| Boc—Phe Phe Sta BmSta—NH₂ | J. Chem. Soc. Chem. Commun: 109, 1985 |
| Naphthylalanyl His Sta-4-amino-1-benzyl piperidine | Kokubu et al., Hypertension: 7(3): 837 (1985) |
| BNMA* His Sta-2(S)-methyl butylamine | Kokubu et al., Hypertension: 7(3): 837 (1985) |
| BNMA Val Sta Isoleucinal | Kokubu et al., Hypertension: 7(3): 837 (1985) |
| 2,3-naphthylalanyl Leu Sta Isoleucinal | Kokubu et al., Hypertension: 7(3): 837 (1985) |
| BNMA Norleucinyl Isoleucinal | Kokubu et al., Hypertension: 7(3): 837 (1985) |

*R indicates reduction of the amide carbonyl to a methylene unit.
*BNMA = beta-naphthyl methyl analyl Another class of renin inhibitors are compounds of the formula

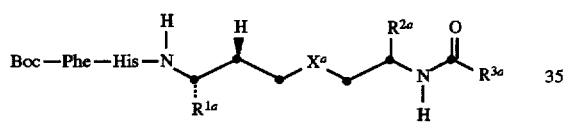

wherein $R^{1a}$ is selected from cyclohexylmethyl, benzyl or butyl, $X^a$ is S or O; $R^{2a}$ is selected from isobutyl, cyclohexylmethyl or benzyl; and $R^{3a}$ is phenethyl. A preferred compound within this class is one wherein $R^{1a}$ is cyclohexylmethyl, $R^{2a}$ is isobutyl, $R^{3a}$ is phenethyl and $X^a$ is S. These compounds are described by Luly et al., Pharmacologist 27(3): 260, 1985, and can be prepared by known techniques from known materials.

Other renin inhibits are disclosed, for example in Szelke et al. U.S. Pat. No. 4,424,207 discloses as having the formula

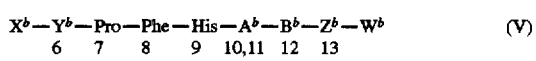

where Pro, Phe and His may be in substituted form;

$X^b$=H; or an acyl or other N-protecting group e.g. acetyl, pivaloyl, t-butyloxycarbonyl (Boc), benzoyl or lower alkyl) primarily $C_1$-$C_5$) or an L or D-amino-acyl residue, which may itself be N-protected similarly;

$Y^b$=D or L-His or other D- or L-basic or aromatic amino-acetyl residue, or is absent;

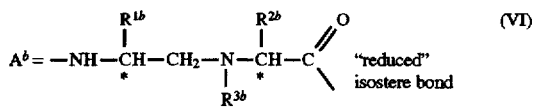

or

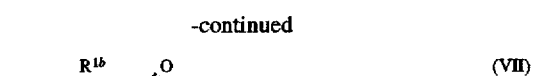

or

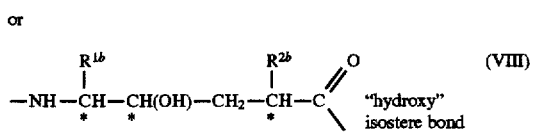

or

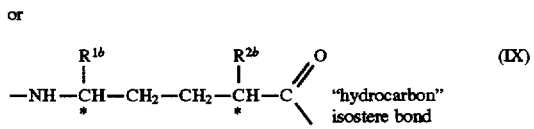

where the configuration at asymmetric centers * is either R or S, where in VIII the hydroxy group may be present as such or protected in ether —$OR^{4b}$ or ester

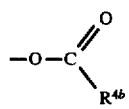

form where $R^{4b}$ is as given under W below and where $R^{1b}$ and $R^b$, the same or different=(Pro(isopropyl), Bu(isobutyl), Bzl(benzyl) or other lipophilic or aromatic amino-acid side chain $R^{3b}$=—H; lower alkyl ($C_1$-$C_5$) or —$SO_2Ph$, —$SO_2C_6H_4CH_3$(p, Boc, formyl or other N-protecting group;

$B^b$=D or L- Val or Ile or other D- or L-lipophilic aminoacyl residue;

$Z^b$=D- or L-tyr, Phe, His or other L- or D-aromatic aminoacyl residue; and $W^b$=

(a) —OH (b) —$OR^{4b}$ where $R^{4b}$=(j), lower alkyl $C_1$–$C_5$(N) cycloalkyl $C_3$–$C_7$ or Bzl (c) —$NH^2$ (d) —$NHR^{3b}$ or —$N(R^5)_2$ wherein $R^{5b}$ is an N-protecting group or $R^{4b}$ (e) L- or D-Lys (f) L- or D-Arg unprotected as the ester or amide (g) L- or D-ser and (h) amino alcohol derived from (e)–(f) as such or protected in ester or ether form $Z^b+W^b$=alcohol derived from
 (i) L-tyr
 (ii) L-Phe
 (iii) D-Tyr or D-Phe
 (iv) His such polypeptide being in the above form or modified by isosteric replacement of one or more remaining peptide bonds by reduced, —$CH_2$—NH—, keto,

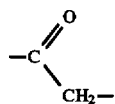

hydroxy, —CH(OH)—$CH_2$—, or hydrocarbon, —$CH_2$—$CH_2$—isosteric links and further being in free form or in protected or salt form at one or more remaining peptide, carboxyl, amino, hydroxy or other reactive groups, in particular as their physiologically acceptable acid addition salts at basic centers.

Veber et al. U.S. Pat. No. 4,479,941 discloses as renin inhibitors compounds of the formula

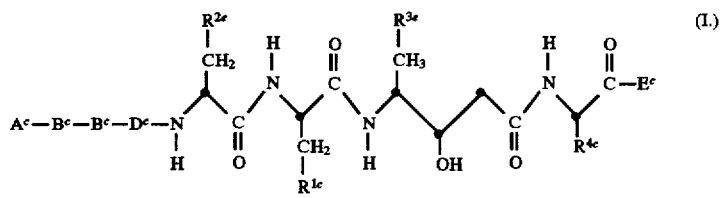

(I.)

wherein:

$A^c$ is hydrogen;

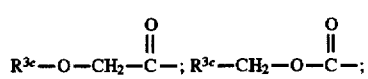

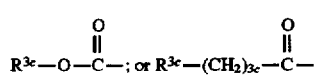

where $n^c$ is 0 to 5 and $R^{3b}$ has the same meaning as set out further below, and may additionally be hydrogen;

$B^c$ is absent; glycyl; sarcosyl; or

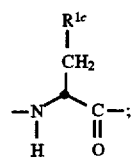

$D^c$ is absent, or

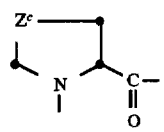

wherein $Z^c$ is ($CH_2$), and $n^c$ is 1 or 2; or —S—;

$R^{1c}$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^{2c}$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^{3c}$ is $C_{3-6}$ alkyl; $C_{3-7}$ cycloalkyl; phenyl; or $C_{3-7}$-cycloalkyl or phenyl mono-substituted with a member selected from the group consisting of methyl, trifluoromethyl, hydroxy, methoxy, fluoro, chloro, bromo, and iodo;

$R^{4c}$ is hydrogen; or

wherein $R^{5c}$ is hydrogen; $C_{1-4}$ alkyl; hydroxy; or $C_{3-7}$ cycloalkyl; and $E^c$ is $$-Y^c-(CH_2)_{n^c}-R_6^c n \qquad (1)$$

where
 $Y^c$ is —NH— or —O—;
 $n^c$ is 0 to 5; and
 $R^{6c}$ is hydrogen; hydroxy; $C_{1-4}$alkyl; $C_{3-7}$cycloalkyl; aryl; aryl substituted with up to five members independently selected from the group consisting of $C_{1-4}$alkyl, trifluoromethyl, hydroxy, $C_{1-4}$alkoxy, amino, mono- or di- $C_{1-4}$ alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl; $C_{1-4}$alkoxy, halo, aryl, aryl $C_{1-4}$alkyl, amino, and mono- or di-$C_{1-4}$alkylamino;

(2)

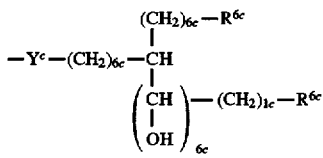

where $Y^c$ is as defined above;

$n^c$ is 0 or 1;

kc is 0 or 1;

lc is 1 to 4;

mc is 1 to 4; and $R^{6c}$ and $R_a^{6c}$ may be the same or different and have the same meaning as $R^{6c}$ above and $R_a^{6c}$ may additionally be

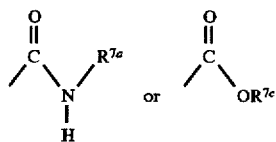

where $R^{7c}$ is hydrogen or $C_{1-3}$alkyl; or (3)

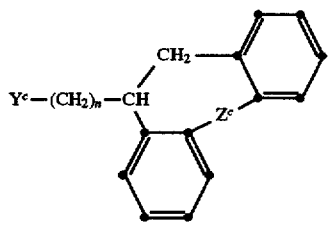

where $Y^c$ is as defined above, nc is 0 or 1; and $Z^c$ is (a) 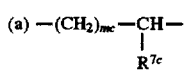

where nc is 0 or 1; and $R^{7c}$ is as defined above; or (b) —(CH$_2$)$_{mc}$—C—
         ‖
         CH$_2$ where nc is 0 or 1;

wherein all of the asymmetric carbon atoms have an S configuration, except for those in the B, D, and E substituents, which may have an S or R configuration; and a pharmaceutically acceptable salt thereof.

Compounds within the class include

IBU[1]—His-Pro-Phe-His-Sta-Leu-benzylamide;
[1]IBU=Iso-butyryl.
IBU—His-Pro-Phe-His-Sta-Leu-2-phenylethylamide;
IBU—His-Pro-Phe-His-Sta-Leu-3-phenylpropylamide;
IBU—His-Pro-Phe-His-Sta-Leu-1,2-diphenylethylamide;
BOC[2]—Phe-His-Sta-Leu(+)[3]-1,2-diphenylethylamide;
[2]BOC=Tert-butyloxycarbonyl.
[3](+) refers to the optical rotation of the amine.
BOC—Phe-His-Sta-Leu-(−)-1,2-diphenylethylamide;
BOC—Phe-His-Sta-Leu-benzylamide;
BOC—Phe-His-Sta-Leu-(+)-α-phenylethylamide;
BOC—Phe-His-Sta-Leu-(−)-α-phenylethylamide;
BOC—Phe-His-Sta-Leu-(+)-α-naphthylethylamide;
BOC—Phe-His-Sta-Leu-(−)-α-naphthylethylamide;
BOC—Phe-His-Sta-Leu-p-chlorobenzylamide;
BOC—Phe-His-Sta-Leu-p-methoxyenzylamide;
BOC—Phe-His-Sta-Leu-10,11-dihydro-5H-dibenzo[a,d]-cycloheptaneamide;
BOC—Phe-His-Sta-Leu-D,L-threo-1,2-diphenyl-2-hydroxyethylamide;
BOC—Phe-His-Sta-Leu-Sta;
BOC—Phe-His-AHPPA[4]-Lleu-benzylamide;
[4]AHPPA=(3S, 4S)-4-amino-3-hydroxy-5-phenylpentanoic acid.
Acetyl—Phe-His-AHPPA-Leu-benzylamide;
BOC—Phe-His-Sta-Leu-(2-amidomethylpyridine);
BOC—Phe-His-Sta-Leu-(4-amidomethylpyridine);
BOC—Phe-His-Sta-Leu-(4-amido-1-benzylpiperidine);
BOC—Phe-His-Sta-Leu-[N-(3-amidopropyl) diethanolamine];
BOC—Phe-His-AHPPA-Leu-(2-amidomethylpyridine);
BOC—Phe-His-ACHPA[5]-Ile-(2-amidomethylpyridine);
[5]ACHPA=(3S, 4S)-4-amino-5-cyclohexyl-3-hydroxypentanoic acid.
IVA[6]-His-D-Pro-Phe-His-ACHPA-Ile-(2-amidomethylpyridine).
[6]IVA=Iso-valeryl.

A preferred compound within this class is BOC-Phe-His-Sta-Leu-(4-amido-1-benzyl-piperidine).

Veber et al. U.S. Pat. No. 4,478,826 discloses as renin inhibitors compounds of the formula

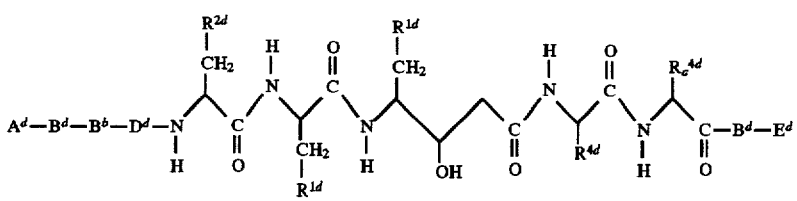

wherein:

$A^d$ is hydrogen;

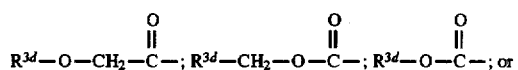

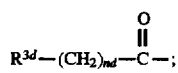

where $n^d$ is 0 to 5 and $R^{3d}$ has the same meaning as set out further below, and may additionally be hydrogen;

$B^d$ is absent; glycyl; sarcosyl; or

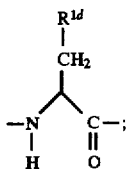

$D^d$ is absent; or

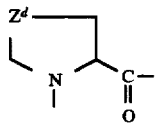

where $Z^d$ is $(CH_2)_{nd}$ and $n^d$ is 1 or 2; or —S—;

$R^{1d}$ is hydrogen; $C_{1-4}$alkyl; hydroxy $C_{1-4}$alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$alkyl; guanidyl $C_{2-3}$ alkyl; or methylthiomethyl;

$R^{2d}$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^{3d}$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

$R^{4d}$ and $R_a^{4d}$ are independently hydrogen; or

where $R^{5d}$ is hydrogen; $C_{1-4}$ alkyl; hydroxy; or $C_{3-7}$ cycloalkyl; and $E^d$ is $OR^d$; $NHR^d$, or $N(R^d)_2$, where each $R^d$ may be the same or different and is hydrogen or $C_{1-4}$ alkyl; wherein all of the asymmetric carbon atoms have an S configuration, except those of substituents $B^d$ and $D^d$, which may also have the R configuration; and a pharmaceutically acceptable salt thereof.

Examples of compounds within the class are tert-Butyloxycarbonyl-His-Pro-Phe-His-Sta-Leu-Leu-Leu-OCH$_3$,
tert-Butyloxycarbonyl-His-Pro-Phe-His-Sta-Leu-Tyr-NH$_2$,
iso-Butyryl-His-Pro-Phe-His-Sta-Leu-Phe-Lys-NH$_2$,
tert-Butyloxycarbonyl-His-Pro-Phe-p-I-Phe-Sta-Leu-Phe-NH$_2$,
iso-Valeryl-His-Pro-Phe-His-Sta-Leu-Val-Phe-NH$_2$,
His-Pro-Phe-His-Sta-Leu-Phe-NH$_2$,
iso-Valeryl-His-Pro-Phe-His-Sta-Leu-Phe-NH$_2$,
Acetyl-Pro-Phe-His-Sta-Leu-Phe-NH$_2$,
Acetyl-Phe-His-Sta-Leu-Phe-NH$_2$,
tert-Butyloxycarbonyl-Phe-His-Sta-Leu-Phe-NH$_2$,
tert-Butyloxycarbonyl-His-Pro-Phe-Phe-Sta-Leu-Phe-NH$_2$,
iso-Butyryl-His-Pro-Phe-His-Sta-Ala-Phe-NH$_2$,

| iso-Butyryl-His—Pro—Phe—His—Sta | { Cyclo-hexyl-Phe—NH$_2$ <br> Ala |
|---|---|

A preferred compound within this class is IVA His Pro Phe His Sta Leu Phe-NH$_2$.

Renin inhibitory activity is disclosed in Veber et al. U.S. Pat. No. 4,384,994 for compounds of the formula

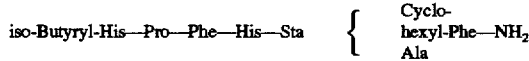

(IV)

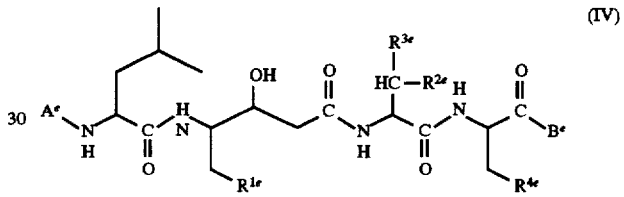

wherein:

$A^e$ is hydrogen; or phenoxyacetyl;

$R^{1e}$ is $C_{3-6}$ straight or branched alkyl; $C_{3-7}$ cycloalkyl; phenyl; or phenyl mono-substituted with hydroxyl, fluoro, chloro, bromo, methyl, or trifluoromethyl;

$R^{2e}$ is hydrogen; or methyl;

$R^{3e}$ is methyl; or isopropyl;

$R^{4e}$ is phenyl; or 4-hydroxyphenyl; and $B^e$ or $OR^e$, $NHR^e$, or $NR_2^e$, where each $R^e$ may be the same or different and is hydrogen or $C_{1-4}$ alkyl;

and a pharmaceutically acceptable salt thereof; all of the asymmetric carbon atoms having an S configuration.

Exemplary are

N-phenoxyacetyl-L-leucyl-(3S,4S)-statyl-L-valyl-L-phenylalanine;
N-phenoxyacetyl-L-leucyl-(3S,4S)-statyl-L-leucyl-L-phenylalanine;
N-phenoxyacetyl-L-leucyl-4(S)-amino-3(S)-hydroxy-5-phenylpentanoyl-L-leucyl-L-phenylalanine;
L-leucyl-(3S,4S)-statyl-L-valyl-L-phenylalanine;
L-leucyl-(3S,4S)-statyl-L-leucyl-L-phenylalanine;
L-leucyl-4(S)-amino-3(S)-hydroxy-5-phenylpentanoyl-L-leucyl-L-phenylalanine; and the amide and $C_{1-4}$ alkyl ester forms of the above peptides.

Boger et al. U.S. Pat. No. 4,485,099 discloses compounds having renin inhibitory activity of the formula

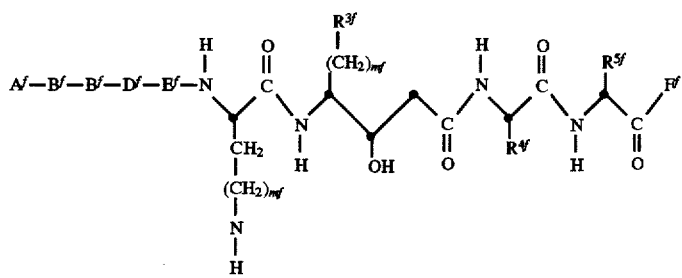 (I)

wherein:

$A^f$ is hydrogen; or

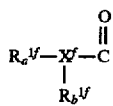

where $X^f$ is

—O—; —O—CH—; —CH—O—; —CH—; —NH—CH—;

or —S—CH—;

and $R_a^{1f}$ and $R_b^{1f}$ may be the same or different and are hydrogen; $Y^f$—$(CH_2)_{pf}$— or $Y^f$—$(CH_2)_{p'f}$—CH=CH—$(CH_2)_{p''f}$, where $Y^f$ is is $C_{1-4}$alkyl; hydrogen; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo;

pf is 0 to 5; and p'f and p"f are independently 0 to 2; except that where $X^f$ is —O—, only one of $R_a^{1f}$ or $R_b^{1f}$ is present;

$B^f$ is absent; glycyl; sarcosyl; or

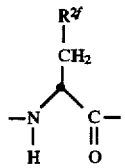

where $R^{2f}$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and; halo; indolyl; 4-imidazolyl; amino $C_{2-4}$alkyl; guanidyl $C_{2-3}$ alkyl; or methylthiomethyl;

$D^f$ is absent; or

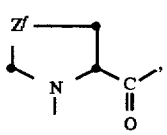

where $Z^f$ is —$(CH_2)_{lf}$— and lf is 1 or 2; or —S—;

$E^f$ is absent; or

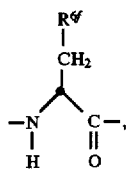

where $R^{6f}$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

$F^f$ is absent; or glycyl;

$R^{3f}$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^{4f}$ is hydrogen; or

where $R^{7f}$ is hydrogen; $C_{1-4}$alkyl; hydroxy; or $C_{3-7}$cycloalkyl; and $R^{6f}$ is as defined above;

$R^{5f}$ is hydrogen;

where $R^{6f}$ and $R^{7f}$ are as defined above; or —$(CH_2)_{qf}$—$R^{8f}$, where qf is 0 or 1–4; and $R^{8f}$ is heterocyclic; heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; guanidyl $C_{2-3}$alkyl; or amino $C_{1-4}$alkyl;

mf is 1 to 4;

nf is 0 to 4; and wherein all of the asymmetric carbon atoms have an S configuration, except for those in the $A^f$, $B^f$ and $D^f$ substituents, which may have an S and R configuration; and a pharmaceutically acceptable salt thereof.

Examples of compounds within this class include

IBU—His—Pro—Phe—Lys—Sta—Leu—Phe⌐
                                    ⌐

-continued

IBU¹—His—Pro—Phe—Orn—Sta—Leu—Phe

IBU—His—Pro—Phe—DAB²—Sta—Leu—Phe—Gly

IBU—His—Pro—Phe—HLys³—Sta—Leu—Phe

IBU—His—Pro—Phe—Orn—Sta—Leu—Phe—Gly

IBU—His—Pro—Phe—Lys—Sta—Leu—Phe—Gly

-continued

BOC⁴—Phe—Lys—Sta—Leu—Phe

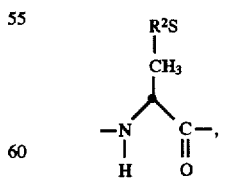

(mixture of isomers)

IVA⁶—His—Pro—Phe—Lys—Sta—Leu—Phe

IVA—His—Pro—Phe—Lys—AHPPA—Leu—Phe

POA⁷—Lys—AHPPA—Leu—Phe

POA—Lys—ACHPA⁸—Ile—His

BOC—Phe—Lys—ACHPA—Ile—His

IVA—His—D—Pro—Phe—Lys—AHPPA—Leu—Phe

IVA—His—D—Pro—Phe—Lys—ACHPA—Leu—Phe

IVA—His—D—Pro—Phe—Lys—ACHPA—Ile—His

-continued

¹IBU = Iso-butyl.
²DAB = 2S-Amino-4-aminobutyric acid.
³HLys = Homolysine, 2S-amino-6-aminoheptanoic acid.
⁴BOC = Tert-butyloxycarbonyl.
⁵AHPPA = (3S, 4S)-4-Amino-3-hydroxy-5-phenyl-pentanoic acid.
⁶IVA = Iso-valeryl.
⁷POA = Phenoxyacetyl.
⁸ACHPA = (3S, 4S)-4-Amino-5-cyclohexyl-3-hydroxy-pentanoic acid.

A preferred compound within this class is

BOC  Phe  Cys  Sta  Leu  Phe.

Renin inhibitory activity is disclosed in Boger et al. U.S. Pat. No. 4,477,441 for compounds of the formula

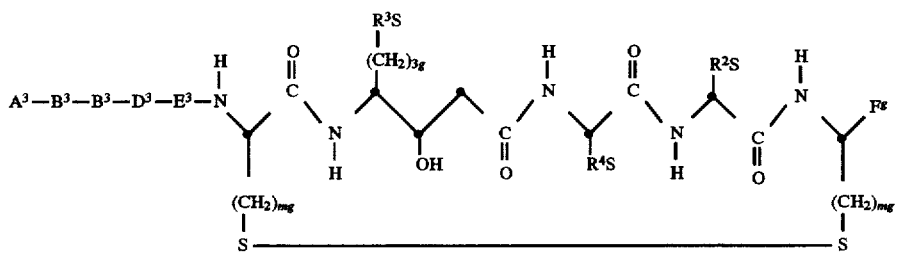

wherein:
$A^g$ is hydrogen; or

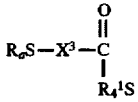

where $X^3$ is —O—;

$$-O-\underset{|}{CH}-; \quad -\underset{|}{CH}-O-; \quad \text{or} \quad -\underset{|}{CH}-;$$

and $R_a^{1g}$ and $R_b^{1g}$ may be the same or different and are hydrogen; $Y^g$—$(CH_2)_{pg}$— or $Y^g$—$(CH_2)_{p'g}$—CH=CH—$(CH_2)_{p''g}$, where $Y^g$ is hydrogen; $C_{1-4}$alkyl; aryl; $C_{3-7}$cycloalkyl; or $C_{3-7}$cycloalkyl or aryl substituted with up to five members independently selected from the group consisting of $C_{1-6}$alkyl, trifluoromethyl, hydroxy, $C_{1-4}$alkoxy, and halo; pg is 0 to 5; and p'g and p41 g are independently 0 to 2; except that where $X^g$ is —O—, only one of $R_a^{1g}$ or $R_b^{1g}$ is present;

$B^g$ is absent; glycyl; sarcosyl; or $$-\underset{\underset{H}{|}}{N}-\underset{\underset{CH_3}{|}}{\overset{\overset{R^{2g}}{|}}{C}}-\underset{\|}{\overset{\|}{C}}-,$$

wherein $R^{2g}$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$ alkyl; guanidyl $C_{2-3}$ alkyl; or methylthiomethyl;

$D^g$ is absent; or

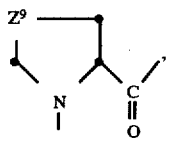

where $Z^g$ is —$(CH_2)_{qg}$— and qg is 1 or 2; or —S—;

$E^g$ is absent; or

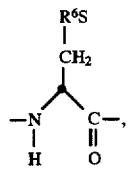

where $R^{6g}$ is hydrogen; $C_{1-4}$alkyl; aryl; aryl $C_{1-4}$alkyl; or aryl $C_{1-4}$alkyl or aryl where the aryl portion is substituted with up to three members selected from the group consisting of $C_{1-4}$alkyl, trifluoromethyl, hydroxy, $C_{1-4}$alkoxy, and halo; or indolyl;

$F^g$ is hydrogen;

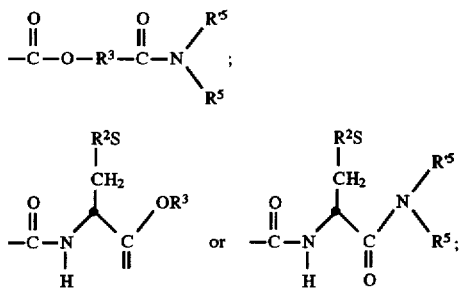

where $R^g$ and $R'^g$ are independently hydrogen or $C_{1-4}$alkyl;

$R^{3g}$ is $C_{3-6}$alkyl; $C_{3-7}$cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^{4g}$ is hydrogen; or

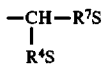

where $R^{7g}$ is hydrogen; $C_{1-4}$alkyl; hydroxy; or $C_{3-7}$cycloalkyl; and $R^{6g}$ is as defined above;

$R^{5g}$ is hydrogen;

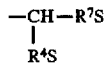

where $R^{6g}$ and $R^{7g}$ are as defined above; or —$(CH_2)_{rg}$—$R^{8g}$, where rg is 0 or 1–4; and $R^{8g}$ is heterocyclic; heterocyclic substituted with up to give members independently selected from the group consisting of $C_{1-6}$alkyl, hydroxy, trifluoromethyl, $C_{1-4}$alkoxy, halo, aryl, aryl $C_{1-4}$alkyl, amino, and mon o- or di-$C_{1-4}$alkylamino; guanidyl $C_{2-3}$alkyl; or amino $C_{1-4}$alkyl;

mg and m'g are independently 1 or 2;

ng is 1 to 4; and wherein all of the asymmetric carbon atoms have an S configuration, except for those in the $A^g$, $B^g$, $D^g$, and $F^g$ substituents, and at the junction of $P^g$, which may have an S or R configuration; and a pharmaceutically acceptable salt thereof.

Compounds within the above class include

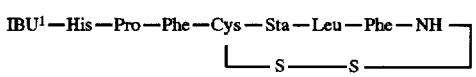

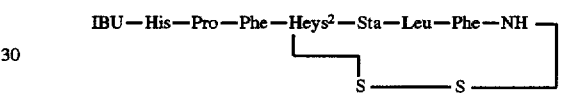

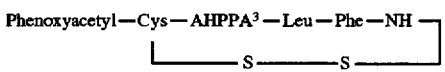

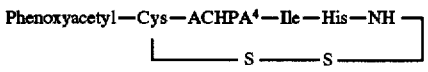

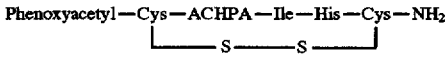

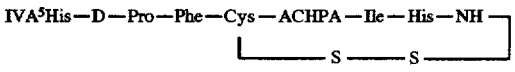

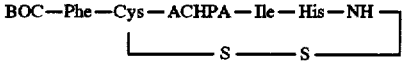

[1]IBU = Iso-butyryl.
[2]Heys = L-homocyclamine
[3]AHPPA = (3S, 4S)-4-Amino-3-hydroxy-5-phenyl-pentanoic acid.
[4]ACHPA = (3S, 4S)-4-Amino-5-cyclohexyl-3-hydroxy-pentanoic acid.
[5]IVA = Iso-valeryl.
[6]BOC = Tert-butyloxycarbonyl.

Boger et al. U.S. Pat. No. 4,477,440 discloses compounds having renin inhibitory activity of the formula

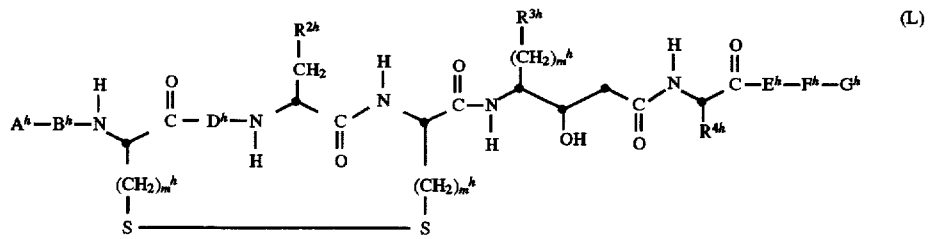

(L)

wherein:

$A^h$ is hydrogen; or $$R_a^{1h}-X^h-\underset{\underset{R_b^{1h}}{|}}{\overset{\overset{O}{\|}}{C}},$$

where $X^h$ is $$-(CH$$
$$-O-;\ -O-CH-;\ -CH-O-;\ \text{or}\ -CH-;$$

and $R_a^{1h}$ and $R_b^{1h}$ may be the same or different and are hydrogen; $Y^h-(CH_2)_n-$ where $Y^h$ is $C_{1-4}$alkyl; hydrogen; aryl; $C_{3-7}$cycloalkyl; or $C_{3-7}$cycloalkyl or aryl substituted with up to five members independently selected from the group consisting of $C_{1-6}$alkyl, trifluoromethyl, hydroxy, $C_{1-4}$alkoxy, and halo; $n^h$ is 0 to 5; except that where $X^h$ is —O—, only one of $R_a^{1h}$ or $R_b^{1h}$ is present;

$B^h$ is absent; glycyl; sarcoxyl; or $$-\underset{\underset{H}{|}}{N}-\overset{\overset{R^{3h}}{|}}{\underset{\|}{\underset{O}{C}}}-,$$
$$\ \ \ \ CH_2$$

where $R^{5h}$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and; halo; indolyl; 4-imidazolyl; amino $C_{2-4}$ alkyl; guanidyl $C_{2-3}$ alkyl; or methylthiomethyl;

$D^h$ is $$\overset{Z^h}{\underset{\underset{O}{\|}}{\underset{N}{\diagdown}}\overset{\diagup}{\underset{\|}{C-}}}$$

where $Z^h$ is $-(CH_2)_p^h-$ and $p^h$ is 1 or 2; or —S—;

$E^h$ is absent; or $$-\underset{\underset{H}{|}}{N}-\overset{\overset{R^{6h}}{|}}{\underset{\|}{\underset{O}{C}}}-,$$

where $R^{6h}$ is hydrogen;

$$-CH-R^{9h},$$
$$\ \ |$$
$$\ \ R^{2h}$$

where $R^{9h}$ is hydrogen, $C_{1-4}$alkyl, hydroxy, or $C_{3-7}$cycloalkyl; or $-CH_2R^{10h}$, where $R^{10h}$ is 4-imidazolyl, amino-$C_{2-4}$alkyl, 2-, 3-, or 4-pyridyl, or guanidyl-$C_{2-3}$alkyl;

$F^h$ is absent; glycyl; sarcosyl; or $$-\underset{\underset{H}{|}}{N}-\overset{\overset{R^{5h}}{|}}{\underset{\|}{\underset{O}{C}}}-,$$
$$\ \ \ \ CH_2$$

where $R^{5h}$ is as defined above;

$G^h$ is $OR^h$; $NHR^h$; $N(R^h)_2$, where each $R^h$ may be the same or different and is hydrogen; or $C_{1-4}$alkyl; or, when $E^h$ and/or $F^h$ are absent; $G^h$ may be (1) $-Y^h-(CH_2)_q{}^h-R^{7h}$ where $Y^h$ is —NH— or —O—; $q^h$ is 0 to 5; and $R^7$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di$C_{1-4}$alkylamino, and halo; amino; mono-, di- or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl-$C_{1-4}$alkyl, amino, and mono- or di-$C_{1-4}$alkylamino;

$$-Y^h-(CH_2)_{kh}-\underset{\underset{OH_{kh}}{|}}{\underset{CH-(CH_2)_{k'h}-R_a^{7h}}{\overset{\overset{(CH_2)_{k''}-R^{7h}}{|}}{CH}}}\ \ \ \ (2)$$

where $Y^h$ is as defined above; $k^h$ is 0 or 1; $k'^h$ is 0 or 1 $k''^h$ is 1 to 4 $k'''^h$ is 1 to 4; $R^{7h}$ and $R_a^{7h}$ may be the same or different and have the same meaning as $R^{7h}$ above and $R_a^{7h}$ may additionally be $$\underset{\underset{H}{|}}{\overset{\overset{O}{\|}}{-C-N-R^{8h}}}\ \text{or}\ {ro}\overset{\overset{O}{\|}}{-C-}OR^{8h}$$

where $R^{8h}$ is hydrogen or $C_{1-3}$alkyl; or (3)

$$Y^h-(CH_2)_r{}^h-CH\diagup\diagdown$$

(with phenyl rings and $Z^h$ linkage)

where $Y^h$ is as defined above; $r^h$ is 0 or 1; and $Z^h$ is $$-(CH_2)_{s}{}^h-CH-,$$ (a)
$$\ \ \ \ \ \ \ \ \ \ \ \ |$$
$$\ \ \ \ \ \ \ \ \ \ \ \ R^{ah}$$

where $r'^h$ is 0 or 1; $R^{8h}$ is as defined above; or

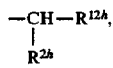

where $r''^h$ is 0 or 1;

$R^{2h}$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^{3h}$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^{4h}$ is hydrogen; or

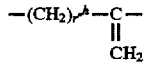 (b)

where $R^{11h}$ is hydrogen; $C_{1-4}$alkyl; hydroxy; or $C_{3-7}$cycloalkyl; and $R^{2h}$ is as defined above; and $m^h$ is 1 or 2;

$m'^h$ is 1 or 2;

$m''^h$ is 1 to 4; and wherein all of the asymmetric carbon atoms have an S configuration, except for those in the $A^h$, $B^h$, $D^h$, $F^h$, and $G^h$ substituents; which may have an S or R configuration; and a pharmaceutically acceptable salt thereof.

Exemplary of compounds within this class are

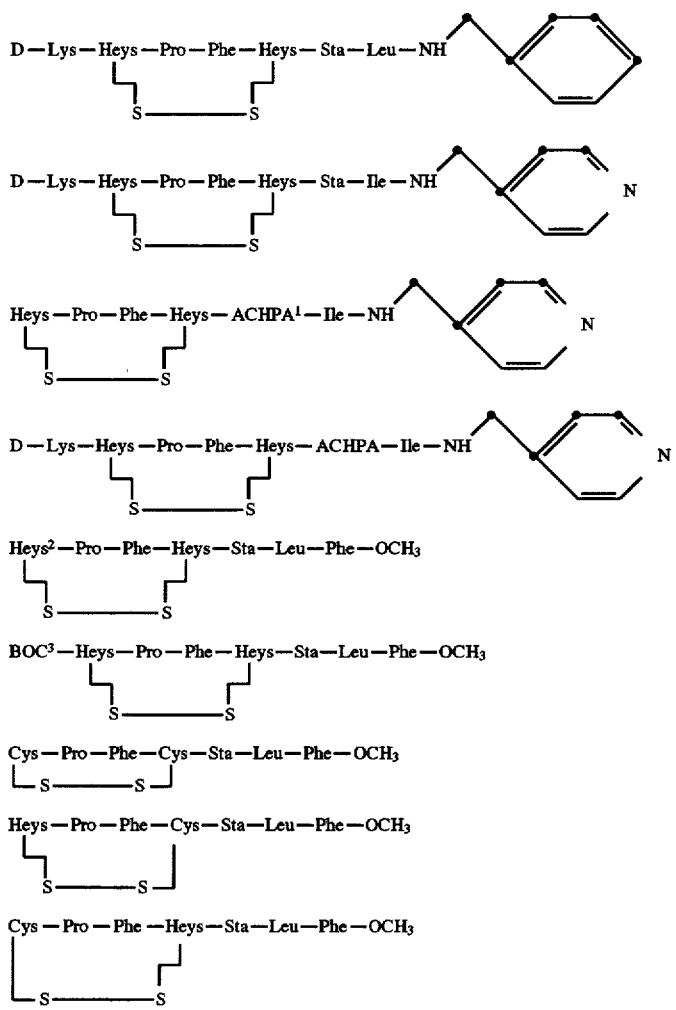

[1]ACHPA = (3S, 4S)-4-amino-5-cyclohexyl-3-hydroxypentanoic acid.
[2]Heys = L-homolysine.
[3]BOC = Tert-butyloxycarbonyl.

Renin inhibitory peptides of the formula are disclosed in Boger et al. U.S. Pat. No. 4,470,971 wherein:

A$^i$ is hydrogen;

$$R^{3i'}-O-CH_2-\overset{O}{\underset{\|}{C}}-;\ R^{3i''}-CH_2-O-\overset{O}{\underset{\|}{C}}-;\ R^{3i''}-O-\overset{O}{\underset{\|}{C}}-;$$

$$\text{or } R^{3i}-(CH_2)_{n2}-\overset{O}{\underset{\|}{C}}-,$$

where ni is 0 to 5 and R$^{3i}$ has the same meaning as set out further below, and may additionally be hydrogen;

B$^i$ is absent; glycyl; sarcosyl; or structure with R$^{1i}$-CH$_2$ group attached to N-H and C=O;

D$^i$ is absent; or structure with Z$^j$ ring attached to N and C=O;

where Z$^i$ is (CH$_2$)$_{ni}$ and ni is 1 or 2; or —S—;

R$^{1i}$ is hydrogen; C$_{1-4}$ alkyl; hydroxy C$_{1-4}$ alkyl; phenyl; phenyl mono-substituted with a member selected from the group consistin of methyl, trifluoromethyl, hydroxy, methoxy, fluoro, chloro, bromo, and iodo; indolyl; 4-imidazolyl; amine C$_{2-4}$ alkyl; guanidyl C$_{2-3}$ alkyl; or methylthiomethyl;

R$^{2i}$ is hydrogen C$_{1-4}$; alkyl; phenyl; phenyl mono-substituted with a member selected from the group consisting of methyl, trifluoromethyl, hydroxy, methoxy, fluoro, chloro, bromo, and iodo; or indolyl;

R$^{3i}$ is C$_{3-6}$ alkyl; C$_{3-7}$ cycloalkyl; phenyl; or phenyl mono-substituted with a member selected from the group consisting of methyl, trifluoromethyl, hydroxy, methoxy, fluoro, chloro, bromo, and iodo;

R$^{4i}$ is hydrogen; or $$\overset{CH-R^{1i}}{\underset{R^{2i}}{|}}$$

where R$'^i$ is hydrogen; C$_{1-4}$ alkyl; hydroxy; or C$_{3-7}$ cycloalkyl;

R$^{5i}$ is 4-imidazolyl; amino C$_{2-4}$ alkyl; 2-, 3-, or 4-pyridyl; or guanidyl C$_{2-3}$ alkyl; and E$^i$ is OR$'''^i$, NHR$'''^i$, or N(R$'''^i$)$_2$, where each R$'''^i$ may be the same or different and is h ydrogen or C$_{1-4}$ alkyl;

wherein all of the asymmetric carbon atoms have an S configuration, except those of substituents B$^i$ and D$^i$, which may also have the R configuration; and a pharmaceutically acceptable salt thereof.

Exemplary are iso-Butyryl-His-Pro-Phe-His-Sta-Val-His-Gly-NH$_2$
iso-Butyryl-His-Pro-Phe-His-Sta-Ile-His-NH$_2$
tert-Butyloxycarbonyl-Phe-His-Sta-Ile-His-NH$_2$
Benzyloxycarbonyl-Phe-His-Sta-Ile-His-NH$_2$
iso-Valeryl-His-Pro-Phe-His-Sta-Ile-His-NH$_2$
iso-Valeryl-His-Pro-Phe-His-Sta-Leu-His-NH$_2$ A preferred compound within this class is IVA-His-Pro-Phe-His-Sta-Ile-His-NH$_2$.

Cazaubon et al. U.S. Pat. No. 4,481,192 discloses renin inhibitors of the formula $$R^j-X^j-Y^j-Statyl_1-Ala-Statyl_2-R'^j \quad (1)$$

in which Statyl$_1$ denotes the radical derived from the aminoacid statine, namely:

$$-NH-CH-CHOC-CH_2-\overset{O}{\underset{\|}{C}}-$$
with CH$_2$-CH(H$_3$C)(CH$_3$) side chain, 3S, 4S isomer and Statyl$_2$ denotes the statyl radical derived from the same aminoacid, but can be the 3S,4S isomer or the 3R,4Sisomer.

R$^j$ denotes a hydrogen atom or an acylating group attached to the terminal amino group of the aminoacid X$^j$—.

More particularly, R$^j$ can represent the following groups: acetyl (Ac), isovaleryl (iva), octyl, t-butylacetyl, t-butoxycarbonyl (Boc) adamantyloxycarbonyl (Adoc), benzyloxycarbonyl (Z), (benzyloxycarbonyl)-β-aminoethylsulphonyl (Z-Tau), (t-butoxycarbonyl)-β-amino-β ethylsulphonyl (Boc-Tau), phenylsulphonyl, benzylsulphonyl or 3-phenylpropionyl.

X$^j$ and Y$^j$, which are identical or different, denote aminoacids of the L or D connfiguration when a centre of asymmetry exists in the molecule, and optionally protected in their side chain.

A preferred compound within this class is BOC Phe His Sta Ala Sta-OMe.

Renin inhibitors of the formula $$Z^k\text{-His-Pro-Phe-His-}X^k\text{-}X^k\text{-Val-Tyr-(D-)-}Y^k \quad (2)$$

are disclosed in Haber et al. U.S. Pat. No. 4,478,827 wherein His is histidine, Pro is proline, Phe is phenylalanine, Val is valine and Tyr is tyrosine. The X$^k$3 are the same or different and are an aromatic or aliphatic amino acid. These may be selected from the group consisting of phenylalanine, a chlorinated phenylalanine such as chlorophenylalanine, dichlorophenylalanine, tyrosine, leucine, glycine, isoleucine, valine or the like. $Y^k$ is a charged amino acid residue at the C-terminus of the polypeptide which can be either positively or negatively charged including lysine, arginine, ornithine, aspartic or glutamic acid and their α-carbon esters of lower aliphatic alcohols ($C_1$–$C_6$) and their primary or secondary lower ($C_1$–$C_6$) aliphatic amides. This charged amine acid residue has the effect of both extending the half-life of the polypeptide molecule in vivo and increasing its solubility, thereby to render the polypeptide effective in inhibiting renin in vivo. $Z^k$ can be either proline, hydroxyproline, thioprline or polyproline having up to about 5 prolyl residues in series.

Exemplary are:
Pro-His-Pro-Phe-His-Phe-Phe-Val-Tyr-D-Lys
Pro-His-Pro-Phe-His-Leu-Phe(Cl)-Val-Tyr-D-Lys
Pro-His-Pro-Phe-His-Leu-Tyr-Val-Tyr-D-Lys
Pro-His-Pro-Phe-His-Leu-Phe-Val-Tyr-D-Lys Hansen, Jr. et al. U.S. Pat. No. 4,510,085 discloses compounds of the formula

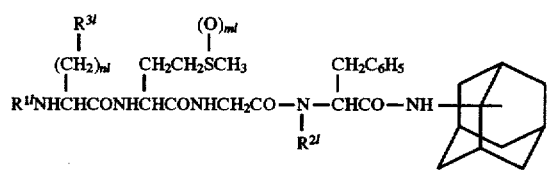

as having renin inhibitory activity
wherein $R^{1l}$ is:

(a) hydrogen; or (b) alkyl or 1 to 6 carbon atoms, inclusive:
wherein $R^{2l}$ is:

(a) hydrogen; or (b) alkyl of 1 to 6 carbon atoms, inclusive:
wherein $R^{3l}$ is:

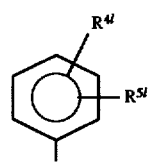

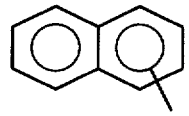

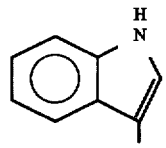

wherein $R^{4l}$ and $R^{5l}$, each being the same or different, are:

(a) hydrogen;

(b) alkyl of 1 to 6 carbon atoms, inclusive; or (c) halogen;
wherein ml is 0, 1 or 2,
wherein nl is 0 or an integer of from 1 to 4; and the pharmaceutically acceptable salts thereof.

Tetrapeptide adamantyl amides are disclosed in U.S. Pat. No. 4,514,332 as having renin inhibitory activity. These compounds are of the formula

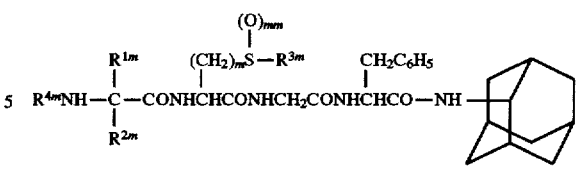

wherein $R^{1m}$ is:

(a)

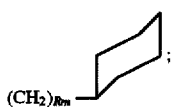

or (b) straight or branched chain alkyls of 1 to 6 carbon atoms, inclusive;
wherein $R^{2m}$ is:

(a) hydrogen; or (b) alkyl of 1 to 3 carbon atoms, inclusive;
wherein $R^{3m}$ is:

(a) $CH_2C_6H_5$; or (b) alkyl of 1 to 3 carbon atoms, inclusive;
wherein $R^{4m}$ is:

(a) hydrogen; or (b) alkyl of 1 to 6 carbon atoms, inclusive;
wherein $m^m$ is 0, 1, or 2;
wherein $n^m$ is 1 or 2;
wherein $p^m$ is 0, 1, or 2;
and the stereochemical configuration of each of the optically active amino acid residues may independently be D, L or DL; and the pharmacologically acceptable salts thereof.

Burton U.S. Pat. No. 4,455,303 discloses as having renin inhibitory activity compound of the formula (a)    H—$A^n$—$B^n$—$C^n$—$D^n$—$E^n$—$OX^n$ wherein $A^n$, $B^n$, $D^n$ are the same or different amino acid residues selected from the group consisting of: Phe, Phe (4-Cl), Tyr, Phe (4-I) and Tyr (ortho-Me)

(b)  $C^n$ is Val, Thr or threo-α-amino-3-chlorobutyric acid;

$E^n$ is lysine or arginine;

$X^n$ is $NH_2$, OH, or $OM^n$, where $M^n$ is a physiologically acceptable cation;

(c) or addition salts of said pentapeptide.

Examples of such compounds include
$H_2$N-Phe-Phe-Val-Tyr-Lys-$CONH_2$
$H_2$N-Tyr-Phe-Val-Tyr-Lys-$CONH_2$
$H_2$N-Phe(4Cl)-Phe-Val-Tyr-Lys-$CONH_2$
$H_2$N-Phe-Tyr-Val-Tyr-Lys-$CONH_2$
$H_2$N-Phe-Phe(4Cl)-Val-Tyr-Lys-$CONH_2$
$H_2$N-Phe-Tyr(Me)-Val-Tyr-Lys-$CONH_2$
$H_2$N-Phe-Phe(4Cl)-Val-Tyr-Lys-$CONH_2$
$H_2$N-Phe-Phe-Thr-Tyr-Lys-$CONH_2$
$H_2$N-Phe-Phe-Bca-Tyr-Lys-$CONH_2$
$H_2$N-Phe-Phe-Val-Phe-Lys-$CONH_2$
$H_2$N-Phe-Phe-Val-Phe(4Cl)-Lys-$CONH_2$ Renin inhibitors are also disclosed in Burton et al. U.S. Pat. No. 4,269,827 as having the formula $Z^p$-His-Pro-Phe-His-$X^p$-$X^p$-Val-Tyr-$Y^p$       Formula 1 wherein His is histidine, Pro is proline, Phe is phenylalanine, Val is valine and Tyr is tyrosine. The $X^p$s are the same or different and are an aromatic or aliphatic amino acid selected from the group consisting of phenylalanine, a chlorinated phenylalanine such as chlorophenylalanine, dichlorophenylalanine, leucine, isoleucine, valine or the like or tyrosine. $Y^p$ is a charged amino acid residue at the C-terminus of the polypeptide which can be either positively or negatively charged including lysine, arginine, ornithine or aspartic acid. This charged amino acid residue has the effect of both extending the half-life of the polypeptide molecule in vivo and increasing the solubility thereby to render the polypeptide effective in inhibiting renin in vivo. $Z^p$ can be either proline or polyproline having up to about 5 prolyl residues in series.

Examples are
Pro-His-Pro-Phe-His-Phe-Phe-Val-Tyr-Lys
Pro-His-Pro-Phe-His-Leu-ClPhe-Val-Tyr-Lys
Pro-His-Pro-Phe-His-Leu-Tyr-Val-Tyr-Lys
Pro-His-Pro-Phe-His-Leu-Phe-Val-Tyr-Lys Castro et al. U.S. Pat. No. 4,185,096 discloses compounds of the formula

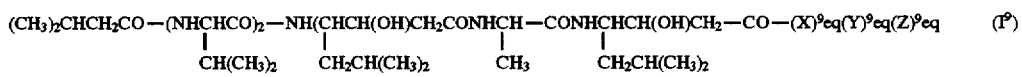

their salts, as having renin inhibitory activity.

In the general formula (I)$^q$ each of the symbols $X^q$, $Y^q$ and $Z^q$ which are identical or different, represent an amino-acid residue selected from arginine, gllutamic acid, aspartic acid, lysine, histidine or valine, forming with the free carboxyl group of the pepstatin or of the adjacent amino-acid a peptide bond-CONH—; the carboxyl function of the terminal amino-acid may exist in free form or in the form of an ester of an aliphatic alcohol containing 1 to 4 carbon atoms, and the indices aq, bq, and cq are each eaual to zero or 1, the sum aq+bq+cq being equal to 1, 2 or 3.

Hayaski et al. U.S. Pat. No. 3,985,875 discloses as having renin inhibitory activity compounds of the formula

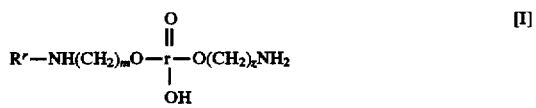

wherein $R^r$ is an octadeca-9,12-dienoyl, octadeca-9,12,15-trienoyl, 4-(4'-chlorophenoxy)phenoxyacetyl or α-[4-(4-40-chlorophenoxy)phenoxyl]propionyl group, and mr is 2 or 3 or their pharmaceutically acceptable acid addition salts;

The above descriptions on pages 3–30 inclusive hereof of classes or renin inhibitors as for use in the present invention were taken from the noted patents and publications or abstracts thereof. Reference should be made to such patents and publications themselves for their full disclosures of such classes and specific compounds within such classes, such patents and publications being incorporated herein by reference for such purposes, and as to any typographical errors or the like which may have occurred in transcription. Also, in describing such renin inhibitors the superscript letters a–r (the letter "o" having been omitted) were included to distinguish among the various classes of compounds and the variable substituent groups thereof.

It is believed that any renin inhibitor will possess the novel utility described herein; however, for purposes of the present invention the preferred renin inhibitors are compounds which are capable of inhibiting the action of renin by at least 50% at a concentration of 1 uM or less, and especially preferred renin inhibitors are compounds which are capable of inhibiting the action of renin by at least 50% at a concentration of 10 nM or less, when tested by the following standard method, which is a modification of the procedure described in Burton et al., Biochemistry 14:3892–3989, 1975:

Hog renal renin (0.1 mU), (5–15 U/mg protein) is used to generated angiotensin I (A I) for tetradecapeptide (TDP). (Human renin and human renin substrate or TDP may also be used.) The reaction mixture also consist of 0.5 mM dimercaprol, 0.5 mM hydroxyquinolone, and 1M maleate buffer, pH 6.0, containing 0.5% bovine serum albumin or bring the total volume to 250 ul. Test drugs or known renin inhibitors, e.g., pepstatin, H-108, are added in concentrations of 100 μM and lower. After 30 minutes incubation at 37° C., the tubes are boiled for 5 minutes to stop the enzyme reaction. Enzyme is added to zero time tubes after boiling. Then, 250 μL or 0.1M maleate buffer are added to all tubes after boiling. Tubes are centrifuged for 10 minutes at 2800 rpm (1650 times g) in an IEC Centra-7R centrifuge and the supernatant solutions are decanted into clean tubes. These samples are either stored frozen at −70° C. and then assayed at a later time or assayed immediately using a radioimmunoassay kit to quantify A I generated. Data are expressed % inhibition of renin.

Many renin inhibitors are known in the art and may be prepared by known methods or by variations thereof. The renin inhibitors employed in the invention may exist in isomeric form. The invention contemplates all such isomers both in pure form and admixture, including racemic mixtures and their pharmaceutically acceptable salts.

The pharmaceutical compositions of the invention are administered in the form of opththalmic pharmaceutical compositions adapted for topical administration to the eye; such as solutions, suspensions, ointments and solid inserts. Formulations of the invention may contain the renin inhibitor in an amount of from about 0.00001 to about 1.0 (w/v%) and especially about 0.00001 to 0.1% of medicament. As a unit dosage form, an amount of renin inhibitor from between about 5 ng to about 0.5 mg, preferably 5 ng to 50 ng of the active substance is applied to the human eye.

Where utilized herein, the term "controlling the elevated intraocular pressure" means the regulation, attenuation and modulation of increased intraocular tension, which is the primary diagnostic symptom of the disease glaucoma. The term also means that the diminution, in the otherwise elevated intraocular pressure, obtained by the practice of the invention is maintained for a significant period of time as, for example, between consecutive doses of the composition of the invention.

The renin inhibitors may be employed in the composition and methods of the invention as the sole IOP lowering ingredient or may be used in combination with other mechanistically distinct IOP lowering ingredients such as beta-adrenergic blocking agents, (e.g., timolol). For purposes of the present invention, the term beta-adrenergic blocker means a compound which by binding to beta adrenergic plasma membrane receptors reduces or eliminates sympathetic activity or blocks the effects of exogenously administered catecholoamines or adrenergic drugs. See, for example, Weiner, N., Drugs That inhibit Adrenergic Nerves and Block Adrenergic Receptors, in *The Pharmaceutical Basis of Therapeutics* (ed. A. G. Goodman, L. S. Goodman, A. Gilman), Macmillan Publishing, New York, 1980, 6th ed., pp. 188–197. Examples of preferred beta adrenergic blockers are atenolol (4-[2-hydroxy-3-[(1-methylethyl)amino]-propoxy]benzeneacetamide), metoprolol (1-[4-(2-methoxyethyl) phenoxy]-3-[(1-methylethyl)amino]-2-propanol), nadolol (5-[3[(1,1-dimethylethyl)amino]-2-hydroxypropoxy]-1,2,3,4-tetrahydro-2,3-naphthalenediol), pindolol (1-(1H-indol-4-yloxy)-3-[(1methylethyl)amino]-2-propanol), propranolol (1-[(1-methylethyl)amino]-3-(1-naphthalenyloxy)-2-propanol), timolol (1-[(1,1-dimethylethyl)amino]-3-[(4-morpholinyl-1,2,5-thiadiazol-3yl)oxy]-2-propanol), labetalol (2-hydroxy-5-[1-hydroxy-2-[(1-methyl-3-phenylpropyl)amino]ethyl]-benzamide), betaxolol (1-[4-[2-(cyclopropylmethoxy)ethyl]-phenoxy]-3-[(methylethyl) amino]-2-propanol), carteolol (5-[3-[(1,1-dimethylethyl) amino]-2-hydroxypropoxyl]-3,4-dihydro-2 (1H)-quinolinone), and dilevalol ([R-(R,R)]-2-hydroxy-5-[1-hydroxy-2-[(1-methyl -3-phenylpropyl)amino]ethyl]-benzamide 4-methylbenzenesulfonate salt), and pharmaceutically acceptable salts and isomers thereof.

The usefulness of beta adrenergic blockers for lowering intraocular pressure is known in the art. Thus, the beta adrenergic blocker timolol, is currently approved by the U.S. Food and Drum Administration for topical use as a treatment for glaucoma. It is marketed in two dose strengths, i.e., 0.25% and 0.5%. As previously stated, this agent must be used with caution in a defined patient population because of recognized untoward side effects (see Physicians Desk Reference for Ophthalmology, 11th edition, 1983, p. 126, Medical Economics Co., Inc., Oradell, N.J. 07649).

As one aspect of the present invention, it is contemplated that a reduction in intraocular pressure equivalent to that obtained by use of a beta-blocker, e.g., the approved clinical dose of the beta-blocker timolol, may be obtained by use of a lower dose of beta-blocker when such lower dose is combined with an effective amount of a renin inhibitor in accordance with the present invention. It is anticipated that the use of the diminished dosage of beta-blocker, e.g., timolol, will result in a reduction of severity and frequency of timolol-like related side effects.

For purposes of this combination treatment modality, the beta-blocker and renin inhibitor are preferably administered simultaneously as one composition in one pharmaceutical dosage form. The beta adrenergic blocker may comprise from about 5 µg to about 125 µg of the composition of the invention. The preferred ranges of the components in the composition of the invention in unit dosage form are as follows:

Beta adrenergic blocker: from 5 µg to 125 µg

Renin inhibitor: from 1 ng to 0.1 mg.

The individual dosage requirements, i.e., the amount of each dose and the frequency of administration, may vary depending on the severity of the disease and the response of the patient.

Those skilled in the art will appreciate that the "intraocular pressure reducing concentration" for such combination therapy will consist of a range of concentrations (doses), and that there will be a lower limit to said concentration below which, the present invention will not operate. For purposes of this invention, this lower limit or minimum dosage may be considered to be about 5% of the effective dose (threshold dose) of the particular component. The intraocular pressure reducing concentration that is actually utilised, whether for a renin inhibitor or for a particular beta adrenergic blocker, will depend on, inter alia, the potency of each particular material, the combination being administered and the age, size and condition of the patient being treated as well as on the severity of the disease state.

I also contemplate that the elevation in IOP associated with the clinical ophthalmic and systemic use of anti-inflammatory steroids can be reduced by the administration of a renin inhibitor. In particular, an increase in IOP is most often associated with the administration of steroidal anti-inflammatory agents. Anti-inflammatory steroids include hydrocortisone, cortisone, prednisolone, prednisone, dexamethasone, methylprednisolone, triamcinolone, betamethasone, alclometasone, flunisolide, beclomethasone, clorocortolone, diflorasone, halcinonide, fluocinonide, flucinolone, desoximetasone, medrysone, paramethasone, 9,21-dichloro-17-[(2-furanylcarbonyl)oxy]-11-hydroxy-16a-methyl-pregna-1,4-diene-3,20-dione and fluorometholone, and their pharmaceutically acceptable salts and esters. Preferred steroids are hydrocortisone, prednisolone, dexamethasone, betamethasone, beclomethasone, medrysone and fluoromethalone and their pharmaceutically acceptable salts and esters. This rise in IOP may occur with all modes of administration of the drugs, including systemic (usually oral), local injection (e.g., depot injection), and especially with ophthalmic topical or intravitreal administration. The renin inhibitor may be administered following steroid treatment to lower elevated IOP, or may be co-administered with the steroid to suppress the IOP-raising effect of the steroid while not interfering with the anti-inflammatory activity of the steroid.

It is further contemplated that may possible combination of dosage forms may be used to administer the combination, e.g., oral steroid/topical renin inhibitor, topical steroid/oral renin inhibitor, oral steroid/oral renin inhibitor, topical steroid/topical renin inhibitor, and locally injected steroid/topical renin inhibitor, although a preferred combination comprises a steroid and a topical renin inhibitor. For ophthalmic use, a combination of a topical steroid and a topical renin inhibitor is preferred. More preferred is a topical opthtalmic pharmaceutical dosage form comprising both a steroid and a renin inhibitor. Such compositions or combinations can be employed in a method for reducing and controlling the elevated IOP associated with ophthalmic and system use of steroidal anti-inflammatory agents, which method comprises administering to a mammal effective amounts of a steroid and a renin inhibitor, either separately or in the same pharmaceutical composition.

Since the present invention relates to treatment with a combination of a renin inhibitor and a steroidal anti-inflammatory agent wherein the renin inhibitor and steroid may be administered separately, the invention also relates to combining separate pharmaceutical compositions in kit form, that is, combining two separate units, a renin inhibitor pharmaceutical composition and a steroid pharmaceutical compositions, in a single package. Preferred components of the kit comprise a topical ophthamological renin inhibitor pharmaceutical composition and a pharmaceutically acceptable steroid composition. More preferred components of the kit are a topical ophthamological renin inhibitor pharmaceutical composition and a topical ophthamological steroid pharmaceutical composition. A particular advantage of the more preferred embodiment of the kit resides in the ability to provide a combination of a renin inhibitor composition which can be administered once or twice a day and a steroid composition which may be administered as frequency as once each hour.

While the mechanism by which ocorticosteroids provide anti-inflammatory activity is unknown, their ability to provide relief from inflammatory symptoms is widely recognized. See, for example, Haynes, R. C., Jr., and Murad, F., "Adrenocortisotropic Hormone; Adrenocortical Steroids and Their Synthetic Analogs, Inhibitors of Adrenocortical Steroid Biosynthesis" in *The Pharmacological Basis of*

*Therapeutics* (ed., A. G. Gilman L. S. Goodman, A. Gilman), Macmillan Publishing, New York, 1980, 6th ed., pp. 1470–1492, n.b. pg. 1490–1491.

In this combination treatment modality, topical formulations of the invention may combine the following amounts of each renin inhibitor and steroidal constituent, or each constituent may be administered separately:

Renin inhibitor from about 0.00001 to about 1.0 (w/v %) and especially about 0.00001 to about 0.1% of medicament. As a unit dosage form, an amount of renin inhibitor from between about 5 ng to about 0.5 mg, preferably about 5 ng to about 50 mg, and especially 5 ng to 25 ng of the active component is applied to the human eye. Individual dosage requirements, i.e., the amount of each dose and the frequency of administration, will depend on the potency of the particular renin inhibitor, the severity of the increase in IOP and the response of the patient.

Steroid from about 0.05 to about 1.5 (w/v %) of medicament. As a unit dosage form, an amount of steroid from between 20 µg to 600 µg of the active composition is applied to the human eye. Individual dosage requirements, i.e., the amount of each dose and the frequency of administration will depend on the potency of the particular steroid, the severity of the disease and the response of the patient. Approximate ranges for such steroids are well known to those skilled in the art. The particular steroid selected will determine which renin inhibitor and concentration thereof to select for use in a combination preparation.

In one embodiment of the invention, both active ingredients, i.e., renin inhibitor and steroid, will be administered simultaneously and be contained in one pharmaceutical dosage form, each component being present in the dosage form in its own respective preferred concentration. When the steroid is administered systemically or topically other than in an ophthalmological composition, the concentration of the steroid in the composition and the unit dosage weight may vary considerably, depending as above on such factors as the potency of the steroid, its onset and duration of action as well as the severity of the disease, and the response of the patient. Appropriate dosage ranges for systemic and optical administration of each steroid are well known in the art.

Those skilled in the art will know that for solutions and suspensions, a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain 0.125 mg or 125 µg of active.

The IOP-lowering effects of the compositions employed in the invention may be measured by the procedure described by Watkins et al., J. Ocular Pharmacol. 1 (2):161–168, 1985.

To prepare suitable dosage forms, the active compositions may be conveniently admixed with a non-toxic pharmaceutically acceptable carrier suitable for topical ophthalmologic administration. Typical of such pharmaceutically acceptable carriers are, for example, water, mixtures of water and water-miscible solvents such as lower alkanols or vegetable oils, petroleum based jelly, and including also from 0.5 to 5% by weight of hydroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxypropyl cellulose, hydroxypropylemethyl cellulose; acrylates such as polyacrylic acids salts; ethylacrylates; polyacrylmaides; natural products such as gelatine, alginates, pectins, tragacanth, karaya, chondrus, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, neutralized carboxyl and xanthan gum; and mixtures of these polymers. The pharmaceutical preparation may also contain non-toxic auxiliary substances such as emulsifying, preserving, wetting, bodying agents and the like, and for example, polyethylene glycols 200, 300, 400 and 600; carbowaxes 1,000, 1,500, 4,000, 6,000 and 10,000; and antibacterial components such as quarternary ammonium compounds; phenylmercuric salts known to have cold sterilizing properties and which are non-injurious in use; thimerosal; methyl and propyl paraben; benzyl alcohol; phenyl ethanol; buffering ingredients such as alkali metal chloride, borate, acetate, gluconate buffers; antioxidants such as sodium metabisulfite, butylated hydroxyanisol (BHA), butylated hydroxytoluene (BHT) and the like; and other conventional ingredients such as sorbitan monolaurate, triethanolaminoeoleate, polyoxyethylene sorbitan monopolmitylate, dioctyl alkali metal sulfosuccinate, monothioglyercol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Patent 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include additional therapeutic agents in addition to the renin inhibitor. For example antibiotics, anesthetics as well as other IOP-lowering agents may be present.

The following examples are intended to illustrate, but not to limit, the present invention. In such examples, Compound A refers to BOC-Phe-His-Sta-Leu-(4-amido-1-benzyl-piperidine).

It is contemplated, however, that therapeutically effective amounts of other renin inhibitors as discussed above may be substituted in its place.

EXAMPLE 1

Topical Solution

| Ingredients | mg/ml |
| --- | --- |
| Compound A | 1.0 |
| Dibasic Sodium Phosphate | 10.4 |
| Monobasic Sodium Phosphate | 2.4 |
| Chlorobutanol | 5.0 |
| Hydroxypropyl methylcelluose | 5.0 |
| Sterile Water | q.s. ad 1.0 mL |
| 1.0N NaOH | q.s. ad pH 7.4 |

Mix the ingredients under sterile conditions and using standard techniques to obtain the ophthamological solution.

EXAMPLE 2

Topical Solution

| Ingredients | mg/ml |
| --- | --- |
| Compound A | 1.0 |
| Timolol | 5.0 |
| Dibasic Sodium Phosphate | 10.4 |
| Monobasic Sodium Phosphate | 2.4 |
| Chlorobutanol | 5.0 |
| Hydroxypropyl methylcellulose | 5.0 |
| Sterile Water | q.s. ad 1.0 mL |
| 1.0N NaOH | q.s. ad pH 7.4 |

Mix the ingredients under sterile conditions and using standard techniques to obtain the ophthamological solution.

EXAMPLE 3

Topical Solution

| Ingredients | mg/ml |
| --- | --- |
| Compound A | 1.0 |
| Dexamethasone Sodium Phosphate | 1.0 |
| Dibasic Sodium Phosphate | 10.4 |
| Monobasic Sodium Phosphate | 2.4 |
| Chlorobutano 1 | 5.0 |
| Hydroxypropyl methylcelluose | 5.0 |
| Sterile Water | q.s. ad 1 mL |
| 1.0N NaOH | q.s. ad pH 7.4 |

Mix the ingredients under sterile conditions and using standard techniques to obtain the ophthamological solution.

Again, other renin inhibitors and steroids can be employed in place of those listed in the formulation above, with the particular amounts varying depending on the drugs employed.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

I claim:

1. A method of reducing elevated intraocular pressure in a mammal which comprises topically administering a composition comprising an intraocular pressure reducing amount of a renin inhibitor and a beta adrenergic blocking agent to an eye of said mammal.

2. A method according to claim 1 wherein the beta adrenergic blocking agent is selected from the atenolol, metoprolol, nadolol, pindolol, propanolol, timolol, labetalol, carteolol, betaxolol or dilevalol or pharmaceutically acceptable salts and/or isomers thereof.

3. A method according to claim 1 wherein the beta adrenergic blocking agent is timolol.

\* \* \* \* \*